(12) United States Patent
Barenberg et al.

(10) Patent No.: US 11,957,805 B2
(45) Date of Patent: *Apr. 16, 2024

(54) LIGHT-ACTIVATED CHLORINE DIOXIDE-RELEASING POWDER AND METHOD OF MANUFACTURE

(71) Applicants: Sumner Barenberg, Boston, MA (US); Robert Cameron, Boalsburg, PA (US); Xiao Tian, Wilmington, DE (US)

(72) Inventors: Sumner Barenberg, Boston, MA (US); Robert Cameron, Boalsburg, PA (US); Xiao Tian, Wilmington, DE (US)

(73) Assignee: Phiex Technologies, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/677,419

(22) Filed: Feb. 22, 2022

(65) Prior Publication Data
US 2023/0263923 A1 Aug. 24, 2023

(51) Int. Cl.
| | |
|---|---|
| A61L 2/08 | (2006.01) |
| A01N 25/12 | (2006.01) |
| A01N 59/00 | (2006.01) |
| A01P 1/00 | (2006.01) |
| A23L 3/3409 | (2006.01) |
| A61L 2/23 | (2006.01) |
| C01B 11/02 | (2006.01) |
| A61L 101/02 | (2006.01) |

(52) U.S. Cl.
CPC ............... *A61L 2/23* (2013.01); *A01N 25/12* (2013.01); *A01N 59/00* (2013.01); *A01P 1/00* (2021.08); *A23L 3/34095* (2013.01); *A61L 2/088* (2013.01); *C01B 11/024* (2013.01); *A61L 2101/02* (2020.08); *A61L 2202/11* (2013.01); *A61L 2202/13* (2013.01)

(58) Field of Classification Search
CPC ............... C01B 11/024; A01N 25/12
See application file for complete search history.

(56) References Cited

U.S. PATENT DOCUMENTS

| | | | |
|---|---|---|---|
| 3,591,515 A | 7/1971 | Lovely | |
| 4,689,169 A | 8/1987 | Mason et al. | |
| 5,695,814 A * | 12/1997 | Wellinghoff | ........... C01B 11/024 |
| | | | 428/407 |
| 5,888,528 A | 3/1999 | Wellinghoff et al. | |
| 6,277,408 B1 | 8/2001 | Wellinghoff et al. | |
| 6,605,304 B1 | 8/2003 | Wellinghoff et al. | |
| 6,767,509 B1 | 7/2004 | Griesbach et al. | |
| 7,273,567 B1 | 9/2007 | Wellinghoff et al. | |
| 7,449,194 B2 | 11/2008 | Lelah et al. | |
| 9,533,272 B2 | 1/2017 | Ozawa et al. | |
| 10,112,831 B2 | 10/2018 | Ozawa et al. | |
| 11,071,801 B2 | 7/2021 | Abbott et al. | |
| 11,224,671 B2 | 1/2022 | Abbott et al. | |
| 2001/0006668 A1 | 7/2001 | Brown | |
| 2008/0026029 A1 | 1/2008 | Wellinghoff et al. | |
| 2011/0052726 A1* | 3/2011 | Smith | .................. C11D 3/3761 |
| | | | 252/186.1 |
| 2014/0311094 A1* | 10/2014 | Thompson | ................ A61L 2/20 |
| | | | 156/308.2 |
| 2017/0157904 A1 | 6/2017 | Abbott et al. | |
| 2018/0235246 A1 | 8/2018 | Abbott et al. | |
| 2018/0243456 A1 | 8/2018 | Abbott et al. | |
| 2019/0282516 A1* | 9/2019 | Hayashi | .................. A23L 33/12 |
| 2021/0002515 A1 | 1/2021 | Jain et al. | |

FOREIGN PATENT DOCUMENTS

| | | | |
|---|---|---|---|
| JP | 2004-532112 A | * | 10/2004 |
| WO | 2017/031351 A1 | | 2/2017 |
| WO | 2021/137862 A1 | | 7/2021 |

OTHER PUBLICATIONS

Sigma Aldrich: Sodium Chlorite, 1 pg, 2022.*
Abbasi, R., et al., "Polymeric Films Containing Sodium Chlorite That Release Disinfectant Gas Upon Activation with UV Light," Advanced Functional Materials, 2019, pp. 1-8, vol. 29, No. 7, Article 1804851.
International Search Report and Written Opinion issued for PCT/US2022/025211 dated Jun. 29, 2022, 8 pages.
Jain, R., "Characterization and Design of Biotic/Abiotic Interfaces," A dissertation submitted in partial fulfillment of the requirements for the degree of Doctor of Philosophy (Chemical Engineering) at the University of Wisconsin-Madison, 2014, 267 pages.
Jain, R., et al., "Using Chemoattractants to Lure Bacteria to Contact-Killing Surfaces," Angewandte Chemie (Internatonal Edition in English), 2016, pp. 5698-5702, vol. 55, No. 19.
Jain, R., et al., "Generation of Gaseous ClO2 from Thin Films of Solid NaClO2 by Sequential Exposure to Ultraviolet Light and Moisture," American Chemical Society Applied Materials & Interfaces, 2017, pp. 16594-16603, vol. 9, No. 19.
International Search Report and Written Opinion in PCT/US2023/029528, dated Nov. 8, 2023, 17 pages.

* cited by examiner

*Primary Examiner* — Kyle A Purdy
(74) *Attorney, Agent, or Firm* — Lewis Rice LLC

(57) ABSTRACT

Methods of manufacturing a light-activated powder are provided which provide solid-state generation and release of chlorine dioxide without detectable amounts of any toxic by-products such as chlorine gas, chlorites, or chlorates. The powder need not be exposed to moisture, relative humidity, or an acid before or during exposure of the powder to visible light to generate the gas. The powder can also be prepared under conditions that minimize or prevent decomposition or oxidation of sodium chlorite or premature light activation of the powder during the manufacturing process to maximize its activity.

21 Claims, No Drawings

LIGHT-ACTIVATED CHLORINE DIOXIDE-RELEASING POWDER AND METHOD OF MANUFACTURE

CROSS REFERENCE TO RELATED APPLICATIONS

Not applicable

GOVERNMENT LICENSE RIGHTS

Not applicable.

THE NAMES OF PARTIES TO A JOINT RESEARCH AGREEMENT

Not applicable.

REFERENCE TO A SEQUENCE LISTING, TABLE, OR COMPUTER PROGRAM LISTING APPENDIX SUBMITTED ON A COMPACT DISC AND AN INCORPORATION-BY-REFERENCE OF THE MATERIAL ON A COMPACT DISC

Not applicable.

FIELD OF THE INVENTION

Light-activated powders and methods for their manufacture are provided for use in generating and releasing chlorine dioxide. More specifically, light-activated powders are provided which are capable of solid-state generation and release of chlorine dioxide without detectable amounts of any toxic by-products and which are prepared under conditions to maximize the powder's activity for use in disinfection, sanitation, sterilization, and control of biological or pathogenic contamination

BACKGROUND OF THE INVENTION

Currently, ethylene oxide is used in the sterilization of medical devices and other products. Ethylene oxide is recognized by the U.S. Food and Drug Administration to have potential adverse impacts on the environment and on public health. The FDA is encouraging changes to ethylene oxide sterilization processes and facilities that will reduce the amount of ethylene oxide on medical devices.

Detectable amounts of toxic by-products including chlorine gas, chlorates and/or chlorites have been observed when chlorine dioxide is generated from some conventional chlorine dioxide-generating products.

SUMMARY OF THE INVENTION

One option for reducing the concentration of ethylene oxide on medical devices is to replace ethylene oxide entirely with a different gas manufactured by a process having less impact on the environment and public health.

In a first aspect of the invention, a method is provided for making a light-activated powder for providing solid-state controlled release of chlorine dioxide The method comprises admixing a light-activated catalyst, a base, sodium chlorite, and water to form an aqueous suspension, and spray-drying the suspension at an inlet temperature ranging from about 482 to about 537° C. (900 to 1000° F.) and an outlet temperature of not more than 143° C. (290° F.) to form a powder. The admixing and spray-drying steps are performed in darkness. When exposed to visible light, the powder is capable of generating the solid-state controlled release of chlorine dioxide from the powder in an amount effective for disinfection, sanitation, sterilization without release of detectable amounts of chlorine gas, chlorates and/or chlorites.

The aqueous suspension may include sodium chlorite of 85-99% purity.

When exposed to visible light, the powder is capable of generating the solid-state controlled release of chlorine dioxide from the powder in an amount effective for disinfection, sanitation, sterilization without release of detectable amounts of toxic by-products, such as chlorine gas and/or chlorite, chlorate.

The powder prepared by this method is capable of generating the solid-state controlled release of the chlorine dioxide from the powder without exposing the powder to moisture, relative humidity, or an acid releasing agent before or during the exposure of the powder to visible light. The acid releasing agent is either an acid, a substance that can be hydrolyzed to an acid (i.e., a substance that reacts with the water that diffuses into the powder to form an acid), or a mixture thereof. The hydronium ions resulting from acid hydrolysis, if present, would diffuse through the powder and react with chlorite anions to generate chlorine dioxide.

A light-activated powder is provided as a second aspect of the invention. The light-activated powder is prepared by the methods described in the first aspect of the invention and in the examples. The powder, when exposed to visible light, is capable of generating the solid-state controlled release of chlorine dioxide from the powder in an amount effective for disinfection, sanitation, sterilization without release of detectable amounts of toxic by-products, such as chlorine gas and/or chlorites, chlorates.

Other objects and features will be in part apparent and in part pointed out hereinafter.

BRIEF DESCRIPTION OF THE DRAWINGS

Not applicable.

DESCRIPTION OF THE PREFERRED EMBODIMENTS

Methods of manufacturing a light-activated powder have been discovered which provide solid-state generation and release of chlorine dioxide without detectable amounts of any toxic by-products such as chlorine gas, chlorates and/or chlorites. The methods include inlet spray-drying temperatures much greater than the 180° C. decomposition temperature for sodium chlorite. The chlorine dioxide is generated and released from a "solid state" powder, meaning that the powder does not include sources of moisture that would initiate chlorine dioxide release, such as unbound water or acid. The powder need not be exposed to moisture, relative humidity, or an acid before or during exposure of the powder to visible light to generate the gas. The powder, when exposed to light, is capable of generating and releasing the gas after activation of the catalyst by light and oxidation or reaction of the sodium chlorite.

The powder can be prepared under conditions that minimize or prevent decomposition or oxidation of sodium chlorite or premature light activation of the powder during the manufacturing process to maximize its activity.

As a first aspect of the invention, a method is provided for making a light-activated powder for providing solid-state controlled release of chlorine dioxide The method comprises admixing a light-activated catalyst, a base, sodium chlorite, and water to form an aqueous suspension, and spray-drying the suspension at an inlet temperature ranging from about 482 to about 537° C. (900 to 1000° F.) and an outlet temperature ranging from about 121° C. (250° F.) to about 143° C. (290° F.) to form a powder. The aqueous suspension includes sodium chlorite of 85-99% purity. The admixing and spray-drying steps are performed in darkness.

When exposed to visible light, the powder is capable of generating the solid-state controlled release of chlorine dioxide from the powder in an amount effective for disinfection, without release of detectable amounts of chlorine gas, chlorites, or chlorates.

When the powder is exposed to light such as visible light, the catalyst is activated and the chlorite anions are oxidized or reacted to generate and release chlorine dioxide.

The powder prepared by this method is capable of generating the solid-state controlled release of the chlorine dioxide from the powder without exposing the powder to moisture, relative humidity, or an acid before or during the exposure of the powder to visible light.

In preparing the aqueous suspension in the methods of the invention, a dispersing agent can be admixed with the catalyst, the base, the sodium chlorite and the water. The dispersing agent can reduce agglomeration within the suspension. The dispersing agent can comprise a nonionic surfactant. Examples of nonionic surfactants include, but are not limited to, secondary alcohol ethoxylate, an alkylphenol ethoxylate, an alkyl ethoxylate, an alkyl aryl ethoxylate, a polyethylene oxide-polypropylene oxide block copolymer, a polyethylene glycol ether of a linear alcohol, a reaction product of a fatty acid with ethylene oxide and/or propylene oxide, polyvinyl alcohol, polyvinylpyrrolidone, a copolymer of polyvinyl alcohol and polyvinylpyrrolidone, a copolymer of (meth)acrylic acid and (meth)acrylic acid ester, or a combination thereof.

It is also preferred to maintain the aqueous suspension at a basic pH of from about 9 to about 14, preferably from about 9 to about 11. The pH can be maintained by adjusting the concentration of the base added in forming the aqueous suspension.

The base in the aqueous suspension is believed to stabilize chlorite anions during processing and participate in the electron transfer by producing hydroxyl radicals that aid in oxidation of the anions. The amount of base within the powder can be adjusted to alter the time period of gas release and enhance thermal stability. Up to about 50 wt. % of a base based upon the total weight of the powder may be included. Suitable bases include, but are not limited to, an alkali metal hydroxide such as lithium, sodium or potassium hydroxide, an alkaline-earth metal hydroxide such as calcium or magnesium hydroxide, a hydroxide salt of a transition metal ion, a protonated primary, secondary or tertiary amine, or a quaternary amine such as ammonium hydroxide. Sodium hydroxide is preferred.

In the methods of the invention, the aqueous suspension can be an azeotrope. When the aqueous suspension is an azeotrope, the spray drying inlet temperature can be as great as 537° C. (1000° F.) yet still avoid sodium chlorite decomposition. The azeotrope can comprise a mixture of solvents including, but not limited to, acetone, acetonitrile, acrylonitrile, an alcohol (e.g., ethanol, methanol, isopropanol, tert-butanol), an alkene, an alkane (e.g., hexane, 2-methylpentane), an alkenal, a haloalkane (e.g., dichloromethane, trichlorotrifluoroethane), a nitroalkane (e.g., nitromethane), aniline, a cycloalkane (e.g., cyclopentane, cyclohexane), benzene, an alkylbenzene, a halobenzene, carbon disulfide, carbon tetrachloride, chloroform, epichlorohydrin, an alkylamine, a dialkylamine, an alkyl halide (e.g., methyl iodide, ethyl iodide), an alkyl ether (e.g., isopropyl ether), an alkyl acetate (e.g., methyl acetate), a haloalkene, an alkenyl chloride, trifluoroacetic acid, toluene, xylene, or any combination thereof.

For example, the aqueous suspension can include an azeotrope comprising acetone and one or more solvents comprising ethanol, methanol, isopropanol, tert-butanol, hexane, 2-methylpentane, dichloromethane, trichlorotrifluoroethane, nitromethane, cyclopentane, cyclohexane, carbon disulfide, carbon tetrachloride, chloroform, methyl iodide, ethyl iodide, isopropyl ether, methyl acetate, or trifluoroacetic acid.

The light used to activate the light-activated catalyst of the powder can be sunlight, fluorescent light, incandescent light, or ultraviolet light. Visible light, such as blue light, is a preferred light source. Additives such as UV blockers can also be included in the powder if it is desirable to limit the wavelength range transmitted to the catalyst. Photosensitizers can be added to shift the absorption wavelength of the powder, particularly to shift an ultraviolet absorption wavelength to a visible absorption wavelength to improve activation by room lighting. UV absorbers can be added to the composition to slow the gas generation and release rate.

Light-activated catalysts are generally used to catalyze oxidation and reduction reactions. When a photon is absorbed by the catalyst, an electron is promoted from the valence band to the conduction band, producing a valence band hole. The hole and the electron diffuse to the surface of the catalyst particle where each may chemically react. Valence band holes oxidize adsorbed water molecules at the surface of the catalyst to generate hydroxyl radicals.

Any semiconductor activated by light or a particle or other material incorporating such a semiconductor, can be used as the light-activated catalyst. Such semiconductors are generally metallic, ceramic, inorganic, or polymeric materials prepared by various processes known in the art, such as sintering. Catalysts for use in the invention are commercially available in a wide range of particle sizes from nanoparticles to granules.

The light-activated catalyst in the aqueous suspension can comprise a metal oxide, a metal sulfide, a metal chalcogenide, a metal phosphide, a metal arsenide, a non-metallic semiconductor, a polymeric semiconductor, a photoactive homopolyanion, a photoactive heteropolyion, or a combination thereof. Preferably, the light-activated catalyst comprises a metal oxide.

When the light-activated catalyst is a metal oxide, the metal oxide can comprise, but is not limited to, titanium dioxide, zinc oxide, tungsten trioxide, ruthenium dioxide, iridium dioxide, tin dioxide, strontium titanate, barium titanate, tantalum oxide, calcium titanate, iron (III) oxide, molybdenum trioxide, niobium pentoxide, indium trioxide, cadmium oxide, hafnium oxide, zirconium oxide, manganese dioxide, copper oxide, vanadium pentoxide, chromium trioxide, yttrium trioxide, silver oxide, or $Ti_xZr_{1-x}O_2$ wherein x is between 0 and 1. Transition metal oxides such as titanium dioxide and zinc oxide are preferred because they are chemically stable, non-toxic, inexpensive, exhibit high photocatalytic activity, and are available as nanoparticles useful in preparing transparent formed or extruded plastic products. Preferably, the light-activated catalyst comprises titanium dioxide, and more preferably, rutile titanium dioxide.

Without being bound by any particular theory, it is believed that when the powder manufactured as described herein comprises rutile titanium dioxide, that the titanium dioxide has flat surfaces of high electron density that adsorb atmospheric water. The sorbed water may be, for example, associated water molecules, dissociated hydroxyl groups in direct contact with the surface, or water molecules hydrogen bonded to associated water and structural oxygen atoms at the surface. The sorbed water content can be determined by differential scanning calorimetry. It is also believed that a dispersing agent, if present, may bind to the titanium dioxide and provide a source of hydronium ions. The sorbed water at the surface of the titanium dioxide is then available to generate solid-state release of chlorine dioxide from the powder.

When the catalyst is a metal sulfide, the metal sulfide can comprise cadmium sulfide, zinc sulfide, indium sulfide, copper sulfide, tungsten disulfide, bismuth trisulfide, or zinc cadmium disulfide.

When the catalyst is a metal chalcogenide, the metal chalcogenide can comprise zinc selenide, cadmium selenide, indium selenide, tungsten selenide, or cadmium telluride.

When the catalyst is a non-metallic semiconductor, the non-metallic semiconductor can comprise silicon, silicon carbide, diamond, germanium, germanium dioxide, or germanium telluride.

Other representative catalysts include indium phosphide; gallium arsenide; polyacetylene; a photoactive homopoly anion that comprises $W_{10}O_{32}^{-4}$; or a photoactive heteropoly ion that comprises $XM_{12}O_{40}^{-n}$ or $X_2M_{18}O_{62}^{-7}$ wherein x is Bi, Si, Ge, P or As, M is Mo or W, and n is an integer from 1 to 12.

An inert atmosphere can be used during the method, such as a nitrogen blanket. An inert atmosphere can be present during the entire method, or during the admixing step, the spray-drying step, in collecting the spray-drying product, and/or in storing the spray-drying product.

The aqueous suspension can be prepared by admixing its ingredients in any order of addition. For example, sodium chlorite can be mixed with water and a base to form a solution, solvents may be added to the solution to form an azeotrope, and the light-activated catalyst can be admixed with the solution or azeotrope to form the suspension. Alternatively, the catalyst and solvents can be admixed to form a slurry and sodium chlorite can be added to the slurry to form the suspension, or both the catalyst and sodium chlorite can be mixed with solvents before being admixed to form the suspension. When preparing the suspension, ultrasonic mixing, high-shear mixing, or any conventional homogenizing method can be used.

Once the suspension is formed, it can be spray dried to form a powder by any method known in the art including, for example, any known atomization methods such as nozzles or rotary discs. Typically, the inlet temperature and outlet temperature are maintained at about 482 to about 537° C. (900 to 1000° F.) and outlet temperature ranging from about 121° C. (250° F.) to about 143° C. (290° F.), respectively. The spray drying process generally occurs rapidly (e.g., within up to about 60 seconds). If desired, the powder may then be further dried by any conventional method.

After spray drying to form the powder, the powder can be admixed with a desiccant to protect the powder further from moisture activation. The desiccant can include, but is not limited to, a silica, a silicate such as sodium silicate, sodium metasilicate, sodium sesquisilicate, sodium orthosilicate, a borosilicate, an aluminosilicate, a zeolite, sodium sulfide, or a combination thereof.

The powder can then be packaged in a container that blocks light of a wavelength capable of activating the catalyst.

The powder manufactured by the methods of the invention can comprise between about 50 wt. % and about 99.99 wt. % of the photocatalyst, and between about 0.01 wt. % and about 50 wt. % sodium chlorite; between about 70 wt. % and about 97 wt. % of the light-activated catalyst, and between about 3 wt. % and about 30 wt. % sodium chlorite; or between about 80 wt. % and about 95 wt. % of the light-activated catalyst, and between about 5 wt. % and about 20 wt. % sodium chlorite.

The rate of chlorine dioxide release that is effective for disinfection can range, for example, from about 0.08 ppm/minute to about 8.0 ppm/minute over a period of about 2 to about 72 hours.

As a second aspect of the invention, a light-activated powder is provided. The light-activated powder is prepared by the methods described in the first aspect of the invention and in the examples. The powder, when exposed to visible light, is capable of generating the solid-state controlled release of chlorine dioxide from the powder in an amount effective for disinfection, without release of detectable amounts of chlorine gas and/or chlorite, chlorate.

Applications for the powders are numerous. They can be used in most any environment where exposure to light can occur. The powders can be formed into solids by molding or sintering. The powders can also be impregnated, melt processed, sintered, blended with other powders, or otherwise incorporated into a variety of materials to provide films, fibers, coatings, tablets, resins, polymers, plastics, tubing, membranes, engineered materials, paints, coatings and adhesives for a wide range of end use applications. The powders are particularly useful in preparing any injection-molded products, compression-molded products, thermal-formed (thermo-formed) products, or extrusion-formed products such as cast or blown films. The thermal stability of the powders allows for their use in injection molding processes.

The powders of the invention are preferably incorporated into injection-molded, compression-molded, thermal-formed, or extrusion-formed plastic products by compounding and pelletizing the powder via conventional means and admixing the pellets with a material before the conventional forming or molding process. Suitable materials for forming these products include any polymer, multicomponent polymer such as a copolymer, a terpolymer or an oligomer, and polymer alloys or blends thereof or any wax. Representative polymers include polyolefins such as polyethylene and polypropylene, polyethylene terephthalate, polyvinyl chloride, polyurethanes, metallocene polymers, polyesters, polyacrylic esters, acrylic, polystyrene, polycarbonates, polyamides, polyester amides, ethylene-vinyl acetate copolymers, ethylene-methacrylate copolymers, and polyacetals. Suitable waxes include microcrystalline wax, paraffin wax, and synthetic wax such as chlorinated wax, polyethylene wax, polyethylene glycols and polypropylene glycols. Preferably, the polymer is biodegradable.

The formed or molded products preferably include between about 0.1 and about 70 wt. % of the powder of the invention and between about 30 and about 99.9 wt. % of the material, and more preferably, between about 1 and about 50 wt. % of the powder of the invention and between about 50 and about 99 wt. % of the material, and most preferably, between about 2 and about 50 wt. % of the powder of the invention and between about 50 and about 98 wt. % of the material.

The formed or molded products can be made by any conventional polymer processing method. For example, a powder or powder pellets of the invention and the material can be mixed together in a mixer, such as a Henschel mixer, and fed to an extruder or molding apparatus operated at a temperature not exceeding about 200° C. to form a melt. The melt can be cast-extruded as a film, formed into pellets using dry air cooling on a vibrating conveyer, or formed into a desired shape by conventional injection-molding, thermoforming, or compression-molding methods.

The melt can be applied on a surface as a film by using well-known hot melt, dip coat, spray coat, curtain coat, dry wax, wet wax, and lamination processes. When the powder is in nano-particle form (e.g., 5 to 20 micron diameter), a transparent film may be formed.

Conventional film forming additives can be added to the materials as needed. Such additives include crosslinking agents, UV stabilizers, flame retardants, emulsifiers, compatibilizers, lubricants, antioxidants, colorants, and dyes.

A multilayered composite can be formed to generate a gas within an enclosure formed of the composite. Such a composite includes a gas-generating layer and a barrier layer. The gas-generating layer includes the powder. The barrier layer is adjacent to a surface of the gas-generating layer. The barrier layer is transparent to light such that it transmits the light to the gas-generating layer. However, the barrier layer is impermeable or only semipermeable to the gases generated and released by the gas-generating layer. The gas-generating layer, when exposed to light is capable of generating and releasing chlorine dioxide after activation of the catalyst and oxidation or reaction of the chlorite anions.

Gas-releasing powders, films or other compositions of the invention can be used to retard, kill, prevent or control microbiological contamination or biochemical decomposition on a surface of a material, within the material or in the atmosphere surrounding the material by placing the material adjacent to the composition of the invention, and exposing the composition to light to release chlorine dioxide from the composition into the atmosphere surrounding the material. Microbiological contaminants can include bacteria, viruses, mold, and fungi.

The compositions can also be used to retard, prevent or control biological contamination of an atmosphere by exposing the composition to light to generate and release chlorine dioxide from the composition into the atmosphere surrounding the composition.

As used herein, retarding, preventing, or controlling biological contamination is also referred to as "sanitization," "disinfection" or "sterilization." Biological contamination can include bacteria, viruses such as corona viruses (e.g., SARS-COV-2 and variants thereof such as the Delta or Omicron variants), mold and fungi.

The compositions can also be used to retard, prevent or control biological contamination of a material by placing the material adjacent to the composition, and exposing the composition to light to generate and release chlorine dioxide from the composition into the atmosphere surrounding the material. Chlorine dioxide, for example, is used following biological warfare to deactivate the biological contaminant (e.g., anthrax) or for other military decontamination.

As an example, the powder or any composition containing the powder, such as a film, can be placed into a sealable bag or other container used in sterilizing medical devices, or into a "red bag" used in decontaminating or disinfecting medical waste or personal protective equipment such as masks, gowns and pants. Alternatively, the bag or container can be made from a film containing the powder of the invention.

The chlorine dioxide released by the powder or composition is effective against SARS-COV-2 and variants thereof such as the Delta or Omicron variants.

Since the chlorine dioxide generated by the powders of the invention is dry and not humid, the powder is also effective in disinfecting electronics without corroding the electronics. This can be advantageous in combatting the effects of a pathogen on electronics in a battlefield contamination resulting from the use of biowarfare.

The compositions can also be used to deodorize a surface of a material or the atmosphere surrounding the material or enhance freshness of the material by placing the material adjacent to the composition, and exposing the composition to light to generate and release chlorine dioxide from the composition into the atmosphere surrounding the material.

The compositions can also be used to retard, prevent, inhibit, or control chemotactic attraction of an organism to a material by placing the material adjacent to the composition, and exposing the composition to light to generate and release chlorine dioxide from the composition into the atmosphere surrounding the material.

In the above methods, the surface of the material or the entire material can be impregnated with a powder of the invention or coated with the composition, the composition can be admixed with the material, the composition can be enclosed within a gas-permeable container, or the material and the composition can be enclosed within a container. When the composition is enclosed within a container, the container can be hermetically sealed, or partially sealed such that some gas leaks from the container.

The chlorine dioxide-releasing powder, for example, can be impregnated into containers used to store food products, soap, laundry detergent, documents, clothing, paint, seeds, medical instruments, devices and supplies such as catheters and sutures, personal care products, medical or biological waste, athletic shoes, ostomy bags, footwear, and refuse. Such a powder can also be impregnated into covers for medical, hospital, home or commercial equipment or covers used in storage. A packet, sachet bag, "tea bag" or other gas-permeable container of the powder can be included in a storage container to provide a chlorine dioxide micro-atmosphere upon activation. The chlorine dioxide-releasing powder can also be impregnated into a paper or polymeric material (e.g., a shower mat, shoe inserts or insoles, bandage material, a meat cutting board, a food wrapper, a food packaging tray, a seed packet, or an air filter); incorporated into a wax or polymeric coating applied to paperboard containers or other surfaces; incorporated into films such as packaging films or covers for storage or medical, hospital, home or commercial equipment; formed into porous parts to sterilize water; admixed with a material to create a micro-atmosphere of chlorine dioxide about the material (e.g., soil); or admixed with other powders to kill microorganisms, enhance freshness or deodorize (e.g., foot powders, bath powders, powders for treating soft surfaces such as carpet powders, desiccants for moisture removal).

The powders can also be used to: neutralize malodors, retard, prevent, inhibit or control chemotaxis (i.e., the attraction of a living organism to a chemical substance); or reduce or eliminate bacteria in animal feed and potentially reduce the bacterial load in the intestines of an animal that consumes the feed.

The compositions of the invention effectively release a gas at temperatures generally encountered in the above uses, including refrigeration temperatures. The chlorine dioxide-releasing compositions, for example, can be used in packaging medical supplies, food or other materials that require refrigeration to sterilize or deodorize the materials. The multilayered films including a barrier layer can also be used to form packaging such as used for medical supplies or food. The barrier layer retains the generated gas within the packaging, for example, to enhance shelf life and prevent mold growth in foods or enhance sterilization of medical supplies.

Having described the invention in detail, it will be apparent that modifications and variations are possible without departing from the scope of the invention defined in the appended claims.

EXAMPLES

The following non-limiting examples are provided to illustrate the invention.

Example 1

A liquid slurry was prepared in a blend tank to be spray dried to form a light-activated powder. The blend tank had an agitator that was on during the addition of all of the ingredients. The lighting of the manufacturing area was dimmed to less than 12 lumens.

First, the blend tank was filled with deionized water. Sodium hydroxide (1.2 wt. % of a 50% solution) was added to the water to form a solution. Sodium chlorite powder (3.0 wt. %) was slowly added to the solution, followed by 26.4 wt. % titanium dioxide to form a slurry. The amounts recited are based on the total weight of the liquid slurry before it was spray-dried. The slurry was then transferred to the feed tank to the spray dryer, again fitted with an agitator.

About 57 kg (125 pounds) of the liquid slurry containing the dissolved sodium chlorite, sodium hydroxide, and suspended titanium dioxide was pumped into the spray dryer using a positive displacement pump. The absolute viscosity of the slurry ranged from 950 to 1750 centipoise at 29° C. (85° F.) with a pH of 12.3. Inlet temperature of the spray dryer ranged from 510° C. (950° F.) to 527° C. (980° F.) over the course of the run. The outlet temperature ranged from 121° C. (250° F.) to 124° C. (255° F.). Powder was produced by spray drying the slurry.

The resulting fine, white powder was screened through a 50-micron mesh into a poly-barrel lined with two opaque plastic bags. A perforated hose connected to a nitrogen gas cylinder was inserted into the barrel to promote cooling. The bags and drum were sealed once the temperature decreased to 32° C. (90° F.). Multiple samples of the finished powder were collected throughout the run and tested for chlorine dioxide production when exposed to an LED light strip. Production of more than 25 ppm chlorine dioxide was consistently observed after 30 seconds of exposure of 5 grams of powder to the LED light source.

Example 2

Titanium dioxide (99.9% rutile (Aldrich Chemical)) is mixed with a solution of sodium chlorite (technical grade (Aldrich Chemical)), sodium hydroxide, acetone, a solvent forming an azeotrope with acetone, and water to form a suspension and is immediately spray dried at an inlet temperature ranging from about 482 to about 537° C. (900 to 1000° F.) and an outlet temperature of not more than 143° C. (290° F.) in darkness (less than 12 lumens) and under nitrogen blanket to form a white powder. The powder is put into a jar and monitored with a 0-100 ppm chlorine dioxide electrochemical sensor. Chlorine dioxide is generated and released from the white powder over hours of testing when the powder is exposed to visible light. Gas release is suspended when the powder is maintained in darkness, and is resumed when the powder is exposed to visible light again.

Pellet Formation: The spray-dried powder is compounded into pellets using 2 melt index linear low-density polyethylene (LLDPE) resin (manufactured by Rexene) at a concentration of 20% powder and 80% resin. Manufacture of the pellets occurs in darkness under nitrogen. The pellets are stored in aluminum foil/plastic laminate containers to protect them from exposure to light.

Film Formation: The pellets are blown into film with 2 melt index Rexene LLDPE resin (50% letdown). The resulting film contains about 10 wt. % of the powder. Manufacture of the film occurs in darkness under nitrogen. The film is stored in an aluminum foil/plastic laminate container to protect it from exposure to light.

Photoactivation of Film under Dry Conditions: A film sample is placed in a jar (including desiccant to create 0% relative humidity) with a 0-10 ppm chlorine dioxide electrochemical detector attached to the lid, and covered with aluminum foil for days to exclude light. No chlorine dioxide is generated during that time. Illumination of the sample with ambient fluorescent room lighting causes immediate generation of chlorine dioxide.

Photoactivation of Film with Light Cycling: A 1 g sample of the film was placed in a 500 ml jar with a 0-10 ppm chlorine dioxide electrochemical detector attached to the lid, and covered with aluminum foil for about 10 minutes to exclude light. No chlorine dioxide is generated during that time. Illumination of the sample from about 10 to 30 minutes with ambient fluorescent room lighting causes immediate generation of chlorine dioxide. The film is covered with foil during which time chlorine dioxide is not generated. When the foil is removed and the film is exposed to room light, chlorine dioxide is generated.

Definitions

The term "suitable substituent," as used herein, is intended to mean a chemically acceptable functional group, preferably a moiety that does not negate the activity of the inventive compounds. Such suitable substituents include, but are not limited to halo groups, perfluoroalkyl groups, perfluoroalkoxy groups, alkyl groups, alkenyl groups, alkynyl groups, hydroxy groups, oxo groups, mercapto groups, alkylthio groups, alkoxy groups, aryl or heteroaryl groups, aryloxy or heteroaryloxy groups, aralkyl or heteroaralkyl groups, aralkoxy or heteroaralkoxy groups, HO—(C—O)— groups, heterocyclic groups, cycloalkyl groups, amino groups, alkyl—and dialkylamino groups, carbamoyl groups, alkylcarbonyl groups, alkoxycarbonyl groups, alkylaminocarbonyl groups, dialkylamino carbonyl groups, arylcarbonyl groups, aryloxycarbonyl groups, alkylsulfonyl groups, and arylsulfonyl groups. Those skilled in the art will appreciate that many substituents can be substituted by additional substituents.

The term "alkyl," as used herein, refers to a linear, branched or cyclic hydrocarbon radical, preferably having 1 to 32 carbon atoms (i.e., 1, 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons), and more preferably having 1 to 18 carbon atoms. Alkyl groups include, but are not limited to, methyl, ethyl, n-propyl, isopropyl, n-butyl, iso-butyl, secondary-butyl, and tertiary-butyl. Alkyl groups can be unsubstituted or substituted by one or more suitable substituents.

The term "alkenyl," as used herein, refers to a straight, branched or cyclic hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, more preferably having 1 to 18 carbon atoms, and having one or more carbon-carbon double bonds. Alkenyl groups include, but are not limited to, ethenyl, 1-propenyl, 2-propenyl (allyl), iso-propenyl, 2-methyl-1-propenyl, 1-butenyl, and 2-butenyl. Alkenyl groups can be unsubstituted or substituted by one or more suitable substituents, as defined above.

The term "alkynyl," as used herein, refers to a straight, branched or cyclic hydrocarbon radical, preferably having 2, 3, 4, 5, 6, 7, 8, 9, 10, 11, 12, 13, 14, 15, 16, 17, 18, 19, 20, 21, 22, 23, 24, 25, 26, 27, 28, 39, 30, 31, or 32 carbons, more preferably having 1 to 18 carbon atoms, and having one or more carbon-carbon triple bonds. Alkynyl groups include, but are not limited to, ethynyl, propynyl, and butynyl. Alkynyl groups can be unsubstituted or substituted by one or more suitable substituents, as defined above.

The term "aryl" or "ar," as used herein alone or as part of another group (e.g., aralkyl), means monocyclic, bicyclic, or tricyclic aromatic radicals such as phenyl, naphthyl, tetrahydronaphthyl, indanyl and the like; optionally substituted by one or more suitable substituents, preferably 1 to 5 suitable substituents, as defined above. The term "aryl" also includes heteroaryl.

"Arylalkyl" or "aralkyl" means an aryl group attached to the parent molecule through an alkylene group. The number of carbon atoms in the aryl group and the alkylene group is selected such that there is a total of about 6 to about 18 carbon atoms in the arylalkyl group. A preferred arylalkyl group is benzyl.

The term "cycloalkyl," as used herein, refers to a mono, bicyclic or tricyclic carbocyclic radical (e.g., cyclopropyl, cyclobutyl, cyclopentyl, cyclohexyl, cycloheptyl, cyclooctyl, cyclononyl, cyclopentenyl, cyclohexenyl, bicyclo[2.2.1]heptanyl, bicyclo[3.2.1]octanyl and bicyclo[5.2.0]nonanyl, etc.); optionally containing 1 or 2 double bonds. Cycloalkyl groups can be unsubstituted or substituted by one or more suitable substituents, preferably 1 to 5 suitable substituents, as defined above.

"Darkness" as used herein means that the light intensity is not more than about 129 lux (i.e., 12 foot-candles) to avoid light-activation of the light-activated catalyst.

The term "-ene" as used as a suffix as part of another group denotes a bivalent radical in which a hydrogen atom is removed from each of two terminal carbons of the group, or if the group is cyclic, from each of two different carbon atoms in the ring. For example, alkylene denotes a bivalent alkyl group such as ethylene (—$CH_2CH_2$—) or isopropylene (—$CH_2(CH_3)CH_2$—). For clarity, addition of the -ene suffix is not intended to alter the definition of the principal word other than denoting a bivalent radical. Thus, continuing the example above, alkylene denotes an optionally substituted linear saturated bivalent hydrocarbon radical.

The term "ether" as used herein represents a bivalent (i.e., difunctional) group including at least one ether linkage (i.e., —O—).

The term "heteroaryl," as used herein, refers to a monocyclic, bicyclic, or tricyclic aromatic heterocyclic group containing one or more heteroatoms (e.g., 1 to 3 heteroatoms) selected from O, S and N in the ring(s). Heteroaryl groups include, but are not limited to, pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2, 3-oxadiazolyl), thiadiazolyl (e.g., 1,3,4-thiadiazolyl), quinolyl, isoquinolyl, benzothienyl, benzofuryl, and indolyl. Heteroaryl groups can be unsubstituted or substituted by one or more suitable substituents, preferably 1 to 5 suitable substituents, as defined above.

The term "hydrocarbon" as used herein describes a compound or radical consisting exclusively of the elements carbon and hydrogen.

The term "substituted" means that in the group in question, at least one hydrogen atom bound to a carbon atom is replaced with one or more substituent groups such as hydroxy (—OH), alkylthio, phosphino, amido (—CON(RA)(RB), wherein RA and RB are independently hydrogen, alkyl, or aryl), amino(—N(RA)(RB), wherein RA and RB are independently hydrogen, alkyl, or aryl), halo (fluoro, chloro, bromo, or iodo), silyl, nitro (—NO2), an ether (—ORA wherein RA is alkyl or aryl), an ester (—OC(O)RA wherein RA is alkyl or aryl), keto (—C(O)RA wherein RA is alkyl or aryl), heterocyclo, and the like. When the term "substituted" introduces or follows a list of possible substituted groups, it is intended that the term apply to every member of that group. That is, the phrase "optionally substituted alkyl or aryl" is to be interpreted as "optionally substituted alkyl or optionally substituted aryl." Likewise, the phrase "alkyl or aryl optionally substituted with fluoride" is to be interpreted as "alkyl optionally substituted with fluoride or aryl optionally substituted with fluoride."

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above products and methods without departing from the scope of the invention, it is intended that all matter contained in the above description and shown in the accompanying drawings shall be interpreted as illustrative and not in a limiting sense.

The invention claimed is:

1. A method of making a light-activated powder for providing solid-state controlled release of chlorine dioxide, the method comprising:
   admixing a light-activated catalyst, a base, sodium chlorite, and water to form an aqueous suspension, the aqueous suspension including sodium chlorite of 85-99% purity; and
   spray-drying the suspension at an inlet temperature ranging from about 482 to about 537° C. (900 to 1000° F.) and an outlet temperature of not more than 143° C. (290° F.) to form a powder,
   wherein:
   the powder does not include sources of moisture that could initiate chlorine dioxide release,
   the admixing and spray-drying steps are performed in darkness, and
   when exposed to visible light, the powder is capable of generating the solid-state controlled release of chlorine dioxide from the powder in an amount effective for disinfection, without release of detectable amounts of chlorine gas, chlorates and/or chlorites.

2. The method of claim 1, further comprising admixing a dispersing agent with the catalyst, the base, the sodium chlorite and the water to form the aqueous suspension.

3. The method of claim 2, wherein the dispersing agent comprises a nonionic surfactant.

4. The method of claim 3, wherein the nonionic surfactant comprises a secondary alcohol ethoxylate, an alkylphenol ethoxylate, an alkyl ethoxylate, an alkyl aryl ethoxylate, a polyethylene oxide-polypropylene oxide block copolymer, a polyethylene glycol ether of a linear alcohol, a reaction product of a fatty acid with ethylene oxide and/or propylene oxide, polyvinyl alcohol, polyvinylpyrrolidone, a copolymer of polyvinyl alcohol and polyvinylpyrrolidone, a copolymer of (meth)acrylic acid and (meth)acrylic acid ester, or any combination thereof.

5. The method of claim 1, wherein the pH of the aqueous suspension is from about 9 to about 14.

6. The method of claim 1, wherein the pH of the aqueous suspension is from about 9 to about 11.

7. The method of claim 1, wherein the aqueous suspension is an azeotrope.

8. The method of claim 7, wherein the azeotrope in the aqueous suspension comprises acetone, acetonitrile, acrylonitrile, an alcohol, an alkenol, an alkane, an alkenal, a haloalkane, aniline, a cycloalkane, benzene, an alkylbenzene, a halobenzene, carbon disulfide, carbon tetrachloride, chloroform, epichlorohydrin, an alkylamine, a dialkylamine, an alkyl halide, an alkyl ether, an alkyl acetate, a haloalkene, an alkenyl chloride, toluene, or xylene.

9. The method of claim 7, wherein the azeotrope comprises acetone and one or more solvents comprising ethanol, methanol, isopropanol, tert-butanol, hexane, 2-methylpentane, dichloromethane, trichlorotrifluoroethane, nitromethane, cyclopentane, cyclohexane, carbon disulfide, carbon tetrachloride, chloroform, methyl iodide, ethyl iodide, isopropyl ether, methyl acetate, or trifluoroacetic acid.

10. The method of claim 1, further comprising admixing the powder with a desiccant.

11. The method of claim 10, wherein the desiccant comprises a silica, a silicate, a borosilicate, an aluminosilicate, a zeolite, sodium sulfide, or any combination thereof.

12. The method of claim 1, wherein the catalyst comprises a metal oxide, a metal sulfide, a metal chalcogenide, a metal phosphide, a metal arsenide, a non-metallic semiconductor, a polymeric semiconductor, a photoactive homopoly anion, a photoactive heteropoly ion, or a combination thereof.

13. The method of claim 12, wherein the metal oxide comprises titanium dioxide, zinc oxide, tungsten trioxide, ruthenium dioxide, iridium dioxide, tin dioxide, strontium titanate, barium titanate, tantalum oxide, calcium titanate, iron (III) oxide, molybdenum trioxide, niobium pentoxide, indium trioxide, cadmium oxide, hafnium oxide, zirconium oxide, manganese dioxide, copper oxide, vanadium pentoxide, chromium trioxide, yttrium trioxide, silver oxide, or $Ti_xZr_{1-x}O_2$ wherein x is between 0 and 1; the metal sulfide comprises cadmium sulfide, zinc sulfide, indium sulfide, copper sulfide, tungsten disulfide, bismuth trisulfide, or zinc cadmium disulfide; the metal chalcogenide comprises zinc selenide, cadmium selenide, indium selenide, tungsten selenide, or cadmium telluride; the metal phosphide comprises indium phosphide; the metal arsenide comprises gallium arsenide; the non-metallic semiconductor comprises silicon, silicon carbide, diamond, germanium, germanium dioxide, or germanium telluride; the polymeric semiconductor comprises polyacetylene; the photoactive homopoly anion comprises $W_{10}O_{32}^{-4}$; and the photoactive heteropoly ion comprises $XM_{12}O_{40}^{-n}$ or $X_2M_{18}O_{62}^{-7}$ wherein x is Bi, Si, Ge, P or As, M is Mo or W, and n is an integer from 1 to 12.

14. The method of claim 13, wherein the metal oxide comprises titanium dioxide.

15. The method of claim 14, wherein the titanium dioxide comprises rutile titanium dioxide.

16. The method of claim 1, wherein the powder comprises between about 50 wt. % and about 99.99 wt. % of the light-activated catalyst, and between about 0.01 wt. % and about 50 wt. % sodium chlorite.

17. The method of claim 1, wherein the powder comprises between about 70 wt. % and about 97 wt. % of the light-activated catalyst, and between about 3 wt. % and about 30 wt. % sodium chlorite.

18. The method of claim 1, wherein the powder comprises between about 80 wt. % and about 95 wt. % of the light-activated catalyst, and between about 5 wt. % and about 20 wt. % sodium chlorite.

19. The method of claim 1, wherein the amount effective for disinfection ranges from about 0.08 ppm/minute to about 8.0 ppm/minute over a period of about 2 to about 72 hours.

20. The method of claim 1, wherein the powder is capable of generating the solid-state controlled release of the chlorine dioxide from the powder without exposing the powder to moisture, relative humidity, or an acid before or during the exposure of the powder to visible light.

21. The method of claim 1, wherein the admixing and/or spray drying steps are performed under an inert atmosphere.

* * * * *